United States Patent [19]

Herskovits

[11] Patent Number: 4,465,870

[45] Date of Patent: Aug. 14, 1984

[54] ETHERIFICATION PROCESS WITH SORPTIVE TREATING OF HYDROCARBON RECYCLE STREAM

[75] Inventor: Lily E. Herskovits, Glenview, Ill.

[73] Assignee: UOP Inc., Des Plaines, Ill.

[21] Appl. No.: 387,719

[22] Filed: Jun. 11, 1982

[51] Int. Cl.$^3$ .............................................. C07C 41/06
[52] U.S. Cl. ................... 568/697; 568/699; 502/53
[58] Field of Search .................. 568/697, 699, 917

[56] References Cited

U.S. PATENT DOCUMENTS

| | | | |
|---|---|---|---|
| 2,720,547 | 10/1955 | Wolff et al. | 260/614 |
| 2,882,243 | 4/1959 | Milton | 568/917 |
| 2,882,244 | 4/1959 | Milton | 568/917 |
| 2,943,105 | 6/1960 | Caruthers | 260/450 |
| 3,021,374 | 2/1962 | Radzitzky | 568/917 |
| 3,489,808 | 1/1970 | Eberly, Jr. | 260/674 |
| 3,726,942 | 4/1973 | Louder | 260/683.61 |
| 3,931,350 | 1/1976 | Sparks | 260/671 B |
| 4,098,684 | 7/1978 | Innes | 208/245 |
| 4,118,425 | 10/1978 | Herbstman | 260/614 A |
| 4,204,077 | 5/1980 | Woods et al. | 568/697 |
| 4,219,678 | 8/1980 | Obenaus et al. | 568/697 |
| 4,252,541 | 2/1981 | Herbstman | 44/56 |
| 4,322,565 | 3/1982 | Dotson et al. | 568/699 |
| 4,329,516 | 5/1982 | Al-Muddarris | 568/697 |
| 4,371,718 | 2/1983 | Huston | 568/699 |

FOREIGN PATENT DOCUMENTS

| | | | |
|---|---|---|---|
| 2448521 | 9/1980 | France | 568/697 |
| 50-10561 | 4/1975 | Japan | 568/699 |
| 56-111050 | 9/1981 | Japan | 568/917 |
| 2050379A | 1/1981 | United Kingdom | |

OTHER PUBLICATIONS

Dowex Ion Exchange, Dow Chemical Co., Midland, Michigan 1964, pp. 33, 31.
Chemical & Engineering News, Jun. 25, 1979, pp. 35-36, "New Plants, Processes Set for Octane Booster" by Stephen C. Stinson.
Technical Paper presented at the AIChE 85th National Meeting, Philadelphia, Jun. 4-8, 1978, pp. 271-275, Fritz Obenaus et al.
Oil & Gas Journal, Nov. 10, 1980, pp. 191-197, "Catalytic LPG Dehydrogenation Fits in '80's Outlook" by Roy C. Berg et al.
Hersh, Molecular Sieves, Reinhold Publishing Corporation, New York, 1961, pp. 53-59, 78-79.

*Primary Examiner*—Howard T. Mars
*Attorney, Agent, or Firm*—James R. Hoatson, Jr.; John F. Spears, Jr.; William H. Page II

[57] ABSTRACT

An integrated process for producing ethers, such as methyl tertiary butyl ether, is disclosed. Specific undesired compounds such as water, methanol or the product ether are removed from a hydrocarbon recycle stream withdrawn from the etherification zone by contacting the recycle stream with a solid regenerable sorbent. Preferably, the sorbent does not remove mono- or diolefinic hydrocarbons from the recycle stream. The treated recycle stream is preferably fractionated to yield isobutane passed into a dehydrogenation zone and normal butane which is charged to a butane isomerization zone.

4 Claims, 1 Drawing Figure

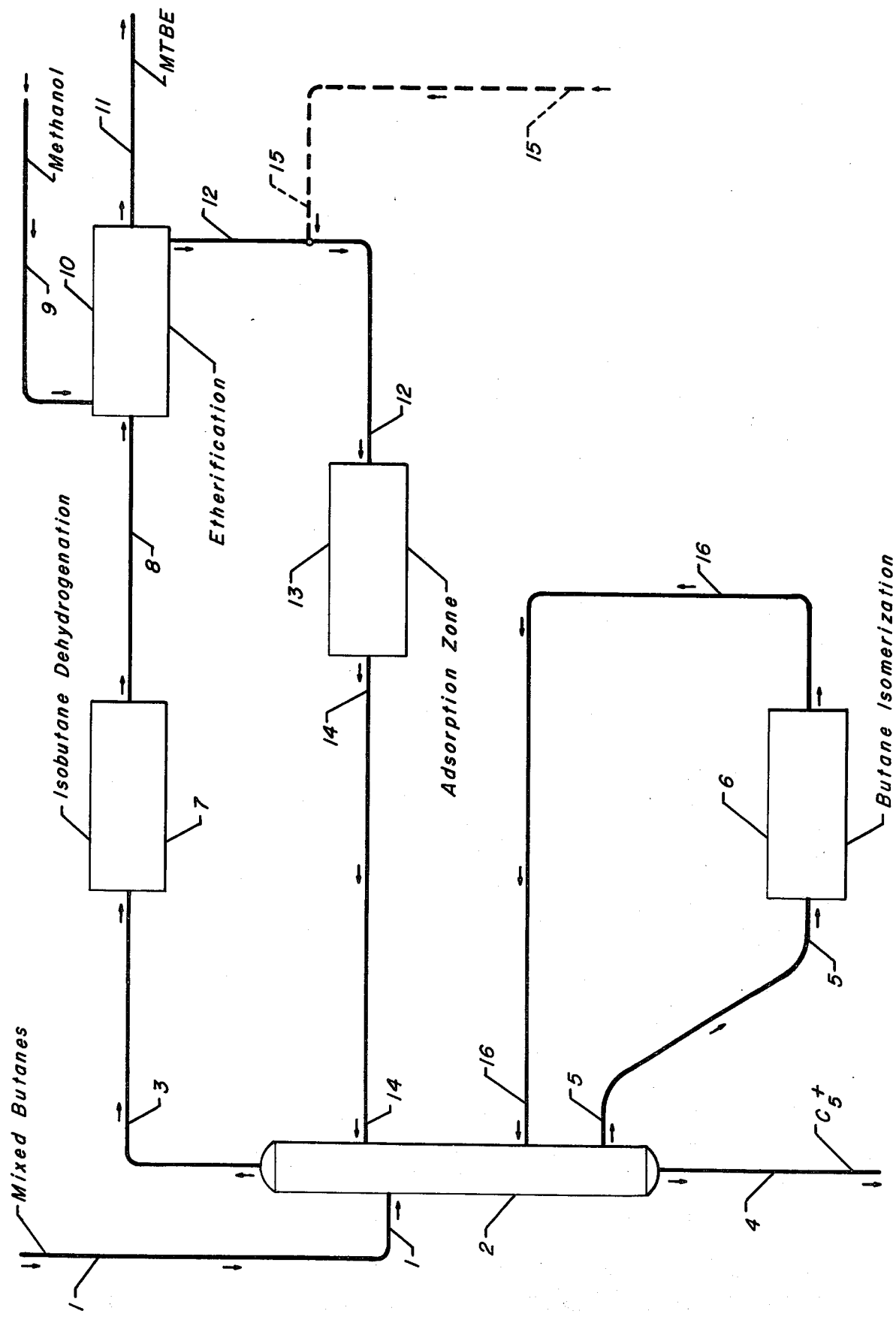

ETHERIFICATION PROCESS WITH SORPTIVE TREATING OF HYDROCARBON RECYCLE STREAM

FIELD OF THE INVENTION

The invention relates to an integrated process for the production of ethers by the reaction of an alcohol with an isoolefin. The invention more directly relates to such an integrated process wherein methyl tertiary butyl ether is produced by the reaction of methanol and isobutylene. The invention specifically relates to the selective removal of oxygen-containing compounds and possibly other undesired compounds from a $C_4$ hydrocarbon recycle stream used in such an integrated process to recycle butanes for the production of additional isobutylene by isomerization and/or dehydrogenation.

PRIOR ART

The production of ethers by the reaction of an isoolefin with an alcohol is well known and is practiced commercially. This highly selective reaction is also used to remove isoolefins, especially isobutylene, from mixed hydrocarbon streams such as the $C_4$ streams produced in steam cracking plants which produce ethylene. Increased attention has been recently focused on ether production due to the rapidly increasing demand for lead-free octane boosters for gasoline such as methyl tertiary butyl ether (MTBE).

A detailed description of processes, including catalysts, processing conditions and product recovery, for the production of MTBE from isobutylene and methanol are provided in U.S. Pat. Nos. 2,720,547 and 4,219,678 in an article at page 35 of the June 25, 1979 edition of *Chemical and Engineering News*. The preferred etherification zone is described in a paper presented at the American Institute of Chemical Engineers 85th National meeting on June 4–8, 1978 by F. Obenaus et al.

Descriptions of integrated processes for producing MTBE, including those which utilize butane isomerization and/or butane dehydrogenation, are found in U.S. Pat. Nos. 3,726,942; 4,118,425 and 4,252,541 and in U.K. Patent Application No. 2,050,379A (priority date May 28, 1979). The last of these references is believed the most pertinent to this application because of the arrangement of the process steps and the similar operation of the various process steps. FIG. 6 of an article at page 191 of the Nov. 10, 1980 edition of *The Oil and Gas Journal* is also pertinent since it presents an integrated process for producing MTBE from mixed butanes having a flow similar to that shown in the subject Drawing. The flow paths of the verious streams are the same in this reference and in the preferred embodiment of the subject process with the exception that a normal butylene hydrogenation zone is shown in place of the adsorption zone of the subject process.

Previously cited U.S. Pat. No. 3,726,942 describes the commonly employed method of removing methanol from the unreacted $C_4$ hydrocarbons separated from the MTBE reaction zone effluent, which is to utilize a water wash. The methanol dissolves in the water and is thus removed from the hydrocarbon stream. The methanol is removed in this reference to reduce the dilution effect on sulfuric acid used in the downstream alkylation step which receives the $C_4$ hydrocarbon stream. This reference (at column 4) also states that an aternative is to use molecular sieves to remove the methanol.

It is also well known to use a solid adsorbent, such as alumina or zeolitic materials, to treat liquid phase hydrocarbon process streams for the removal of small quantities of undesired contaminants. These adsorbents have been used to remove water, sulfur compounds and various hydrocarbonaceous compounds including such oxygenated compounds as alcohols from process streams. This use of adsorbents is taught in U.S. Pat. Nos. 2,943,105; 3,489,808; 3,931,350 and 4,098,684.

BRIEF SUMMARY OF THE INVENTION

The invention provides an improved process for the production of ethers by the reaction of an alcohol and an isoolefin by eliminating the need to hydrotreat a hydrocarbon recycle stream to remove small amounts of alcohol or product ether. This may result in the total elimination of the need for a hydrotreating zone in the integrated process if diolefins may be tolerated or are produced at a low enough rate within the dehydrogenation zone. The improvement resides in the use of a solid sorbent, such as a type 13X molecular sieve, to selectively remove oxygen-containing compounds from the recycle stream. This is an improvement compared to hydrotreating in that both capital and operating costs are reduced.

The invention may be characterized as an integrated process for the production of methyl tertiary butyl ether which comprises the steps of contacting methanol and a mixed hydrocarbon stream comprising normal butane, isobutane and isobutylene with an acidic etherification catalyst in an etherification zone under conditions effective to result in the production of methyl tertiary butyl ether, which is removed in a product stream; withdrawing a recycle stream which is rich in $C_4$ hydrocarbons and comprises isobutane, normal butene, water, butadiene, methanol and methyl tertiary butyl ether from the etherification zone; contacting the recycle stream with a solid adsorbent which removes methanol, dimethyl ether and methyl tertiary butyl ether from the recycle stream; and separating the recycle stream in a fractionation zone into a first stream comprising isobutane which is passed into a dehydrogenation zone to produce isobutylene which is passed into the etherification zone and a second stream comprising normal butane which is passed into an isomerization zone.

BRIEF DESCRIPTION OF THE DRAWING

The drawing illustrates the overall flow in the preferred arrangement of an integrated process to produce MTBE from methanol and a mixture of butanes. The butane feed stream carried by line 1 normally comprises isobutane and normal butane and may also contain isobutylene. This feed stream enters a reboiled fractionation column 2 referred to as the deisobutanizer together with a treated $C_4$ hydrocarbon recycle stream from line 14 and the net butane isomerization zone effluent stream from line 16. Any hydrocarbonaceous compounds having five or more carbon atoms per molecule or other similar high boiling compounds are removed from the column as a net bottoms stream carried by line 4. The deisobutanizer is designed and operated to produce a lower sidecut stream carried by line 5 which has a significantly higher normal butane concentration as compared to any isobutane it may contain. This stream is passed through a catalytic butane isomerization zone 6 to produce additional isobutane which is returned to the deisobutanizer as part of a net isomerization zone effluent stream carried by line 7.

Essentially all of the isobutane which enters the deisobutanizer becomes concentrated into a net overhead stream carried by line 3 which is passed into a catalytic isobutane dehydrogenation zone 7. Passage of the isobutane through this zone results in the production of a net isobutane dehydrogenation zone effluent stream comprising a mixture of isobutane and isobutylene. This stream is passed through line 8 into an etherification zone 10 and contacted with a suitable catalyst in admixture with methanol from line 9 while the reactants are maintained at suitable etherification conditions. The etherification tion zone 10 contains suitable separation facilities, such as two or more fractionation columns, to separate the effluent of the etherification reactor into a net product stream comprising MTBE removed from the process in line 11 and a $C_4$ hydrocarbon recycle stream carried by line 12.

The hydrocarbon recycle stream comprises isobutane and normal butane and possibly small amounts of isobutylene. The separation steps performed in the etherification zone preferably include water washing this stream to remove methanol and other water-soluble compounds. The recycle hydrocarbon stream nevertheless will contain a small amount of methanol and MTBE unless an exorbitant amount of water is used in the washing procedure. These oxygen-containing compounds are preferably removed to prevent damage to the catalysts employed in the isobutylene producing zones of the process. This is preferably accomplished in the subject process by contacting the recycle stream with a solid adsorbent located in the adsorption zone 13, but other sorbents may be employed in this sorption zone. The recycle stream is then passed into the deisobutanizer through line 14. The mixed butane feed stream could alternatively enter the process in optional line 15 and also pass through the adsorption zone.

DETAILED DESCRIPTION

Etherification processes have been constructed or proposed for the production of various ethers as either end products or as intermediates in processes for producing other valuable chemical compounds. For instance, plans have been announced to produce pure isobutane for the manufacture of polyisobutylenes and tert-butylphenol by first producing MTBE and then cracking the MTBE to yield isobutylene and methanol which is recycled. Large amounts of MTBE are also being produced for use as anti-knock compounds in lead-free gasoline.

The majority of the description of the invention is presented in terms of the reaction of isobutylene with methanol to form MTBE since these are the preferred feed materials and the commercially predominant reaction. However, it is not intended to thereby lessen the scope of the inventive concept, which may be applied in the production of other ethers when a similar hydrocarbon recycle stream is present in the process. The inventive concept may therefore be applied in general to the reaction of isoolefins having less than six carbon atoms per molecule with water-soluble alcohols which preferably have less than four carbon atoms per molecule. The next preferred alcohol after methanol is ethanol but other alcohols such as propanols, ethylene glycol or propylene glycol can also be consumed in the process. The isoolefin is preferably derived by dehydrogenation of isobutane or isopentane. The subject process may therefore be employed in the production of a wide variety of ethers other than MTBE including methyl tertiary amyl ether, ethyl tertiary amyl ether and ethyl tertiary butyl ether.

The ethers are produced by the reaction of the alcohol and the isoolefin in an etherification zone. The ethers are then separated from unreacted hydrocarbons, water and unreacted alcohol to yield the ether product stream. In the case of MTBE production, the unreacted hydrocarbons include normal butenes, formed from normal butane which enters the dehydrogenation zone, and possibly various butadienes since these compounds do not react with the alcohol. Also normally present is a larger amount of isobutane from the dehydrogenation zone feed stream which was not dehydrogenated. These unreacted hydrocarbons are withdrawn from the separatory facilities used to recover the ether as a separate hydrocarbon stream.

In the integrated processes to which the subject invention is directed, this separate hydrocarbon stream is recycled to produce more of the isoolefin, normally by the sequential steps of isomerization and dehydrogenation, and is therefore referred to as the hydrocarbon recycle stream. If not removed from the process, normal butenes and any butadienes will accumulate within the recycle stream and cause it to increase in volume. The presence of these compounds also may have detrimental effects on the preferred dehydrogenation catalyst. Other components of the hydrocarbon recycle stream include smaller amounts of various oxygenates such as the product ether, the feed alcohol and oxygen-containing reaction by-products resulting from side reactions and the presence of impurities in the feed streams. It is also not desirable to pass these oxygenates into the isomerization or dehydrogenation zones because of their effects on the preferred catalysts. It is therefore desirable to remove, alter or destroy all of these undesired compounds before the hydrocarbon recycle stream is passed into the isomerization and dehydrogenation zones.

Heretofore it has been the practice to remove undesired compounds from the hydrocarbon recycle stream by hydrotreating. That is the olefins, diolefins and oxygenates were hydrogenated to form paraffins. Hydrotreating the hydrocarbon recycle stream can add considerably to the capital and operating costs of the overall process. It is therefore an objective of the subject invention to reduce or if possible eliminate the need to hydrotreat the hydrocarbon recycle stream of integrated etherification processes. It is another objective of the subject invention to provide a method of removing oxygenated hydrocarbonaceous compounds from the $C_4$ hydrocarbon recycle stream of an integrated process for producing MTBE.

In the subject process oxygen-containing hydrocarbonaceous compounds, and possibly other compounds as described below, are removed from the hydrocarbon recycle stream by contacting the recycle stream with a sorbent solid. The sorbent, which may function as an adsorbent, is preferably disposed as a fixed bed in two or more cylindrical contacting chambers. The flow of the recycle stream is preferably switched between different chambers to allow continuous processing of the recycle stream while the sorbent in the chambers which are not being used is either regenerated or replaced depending on the regenerability and remaining capacity of the sorbent. The sorbent may also be contained in a different chamber configuration such as a moving bed or a fluidized bed.

The required sorption-promoting conditions will depend on such factors as the specific sorbent used in the process and the chemical compounds to be removed from the recycle stream. A general range of suitable sorption-promoting conditions includes a superatmospheric pressure less than about 500 psig, although higher pressures may be employed, and a temperature less than about 160° F. (71° C.). A liquid hourly space velocity of less than 10 hr.$^{-1}$ should be employed. A preferred range of sorption-promoting conditions includes a pressure between 10 and about 200 psig, a temperature between 50° and 150° F. (10° and 65° C.) and a liquid hourly space velocity between 0.3 and 3.0 hr.$^{-1}$.

The sorbent is preferably in the form of solid spherical particles on the order of about 1/16 to ¼ of an inch in diameter. The preferred sorbents are the zeolitic materials known as molecular sieves and ion exchange resins. The selection of sorbents for use in the subject process is therefore dependent on the effectiveness, selectivity and regenerability of the particular solid and is not dependent on the manner in which the sorbent acts to remove the undesired compounds. The sorbent may therefore act by physical or chemical adsorption or by ion exchange. As is known to those skilled in the art these materials are normally selective as to the compounds they tend to sorb, and it is therefore necessary to carefully select the proper materials. Small scale testing may be required in some instances as part of the selection process to determine the appropriateness of materials other than those listed herein. It is contemplated that the solid sorbent may also be chosen from the group consistingg of natural and synthetic aluminas, clays, charcoals and other known sorbents. The preferred adsorbents are type 5A and type 13X molecular sieves which should remove both the oxygen-containing impurities and some sulfur compounds which may be present in the feed stream such as dimethylsulfoxide. A type 3A molecular sieve may be employed to remove water from the recycle hydrocarbon stream.

The regeneration of the sorbents, if the sorbents are regenerable in this manner, preferably includes or consists of a low temperature hydrogen stripping step in which the temperature of the hydrogen stream is gradually increased. The regeneration gas stream preferably contains at least 85 mole percent hydrogen and has an initial temperature below 200° F. (93° C.). The temperature of the gas stream is gradually increased at a rate less than about 50 Fahrenheit degrees until a temperature in excess of about 400°-600° F. (204°-315° C.) is reached. Heated hydrocarbons can be employed if desired as a supplement to this hydrogen treating step to reach higher regeneration temperatures. It is also possible that the low temperature hydrogen stripping step may not be required and that conventional regeneration procedures such as pressure reduction and/or initial high temperature hydrocarbon, steam or nitrogen purging may be employed.

The classification of chemical compounds present in the hydrocarbon recycle stream as undesired compounds or as impurities will depend on such factors as the identity of the reacting alcohol and isoolefin and the susceptibility of the downstream catalyst(s) to poisoning or deactivation by the various compounds. Some of the compounds which it is desired to remove may be derived from the hydrocarbon feed stream if the feed stream is admixed into the recycle stream. However, it is believed that most or all of the compounds which it is desired to remove from the hydrocarbon recycle stream will normally be present in the recycle stream as it leaves the etherification zone. These compounds include the product ether, the feed alcohol and oxygen-containing reaction by-products. In the case of MTBE production these compounds are MTBE, methanol and tertiary butyl alcohol or similar by-products including dimethyl ether. Since the recycle stream is normally water washed to remove the vast majority of the water-soluble compounds including MTBE and methanol, the recycle stream will then contain water and most probably will be saturated. This water may also be removed from the recycle stream, if desired, by the sorbent. The recycle hydrocarbon stream will also contain mono- and diolefins produced in the dehydrogenation zone. In the preferred embodiment these olefins are isobutylene and normal butylene and butadienes. It is preferred that most of the olefinic hydrocarbons present in the recycle stream are not removed during contact with the sorbent. Therefore, preferably less than 5 mole percent of any butadiene present in the recycle stream is removed from the recycle stream by contact with the solid sorbent.

The removal of oxygen-containing compounds from the recycle stream may by itself be sufficient to eliminate any requirement for hydrotreating the recycle stream. This assumes that the olefinic components are at a level which is tolerable in the downstream portion of the overall integrated process either due to a very low concentration of the olefinic compounds in the recycle stream or the ability of the catalysts to function properly with feed streams containing mono- and diolefins. The characteristics of the catalysts will therefore be very significant in determining the required treatment for the recycle stream since the dehydrogenation catalyst's tendency to produce diolefinic hydrocarbons largely determines the concentration of diolefins in the recycle stream. It is believed that destruction of the oxygen-containing compounds by hydrotreating would require significantly more severe operating conditions than mere saturation of the olefinic compounds. Removal of the oxygen-containing compounds from the recycle stream will therefore at least reduce the severity and cost of any recycle stream hydrotreating which may still be required.

In the preferred form of the overall integrated etherification process the net effluent stream of the dehydrogenation zone, which comprises a mixture of olefins and saturated hydrocarbons, is fed to an etherification zone together with the feed alcohol. The etherification zone may take many different forms but is preferably similar to that described in U.S. Pat. No. 4,219,678 and shown in the previously cited paper. In this instance the isobutane or other isoolefin, methanol or other feed alcohol, and a recycle stream containing the product ether, and methanol are passed into the reaction zone in which they are contacted with an acidic catalyst while maintained at etherification conditions. A wide range of materials is known to be effective as etherification catalysts for the preferred reactants including mineral acids such as sulfuric acid, boron trifluoride, phosphoric acid on kieselguhr, phosphorus-modified zeolites and various sulfonated resins. The use of a sulfonated solid resin catalyst is preferred. These resin-type catalysts include the reaction products of phenol-formaldehyde resins and sulfuric acid and sulfonated polystyrene resins including those cross-linked with divinylbenzene. Further information on suitable etherification catalysts may be obtained by reference to U.S. Pat. Nos. 2,480,940; 2,922,822; and 4,270,929 and the previously cited etherification references.

A broad range of etherification conditions includes a superatmospheric pressure sufficient to maintain the reactants as a liquid phase, generally below about 200 psig, and a temperature between about 30° and about 100° C. A preferred temperature range is from 50° to 100° C. The reaction rate is normally faster at higher temperatures but conversion is more complete at lower temperatures. High conversion in a moderate volume reaction zone can therefore be obtained if the initial section of the reaction zone, e.g. the first two-thirds, is maintained above 70° C. and the remainder of the reaction zone is maintained below 50° C. This may be accomplished most easily with two reactors. The ratio of feed alcohol to isoolefin should normally be maintained in the broad range of from 1:1 to 2:1. With the preferred reactants good results are achieved if the ratio of methanol to isobutene is between 1.1:1 and 1.5:1. An excess of methanol above that required to achieve satisfactory conversion at good selectivity should be avoided.

It is preferred that the effluent of the etherification reaction zone is passed into an intermediate point of a fractionation column designed and operated to concentrate unconverted isoolefins present in the effluent into a net overhead stream. In the case of isobutene being the isoolefin, this column is a deisobutanizer. The net overhead stream of this column becomes the recycle hydrocarbon stream of the subject process and is passed into the sorption zone, preferably after passage through a water wash zone to recover most of the methanol or other alcohol present in this stream. The bottoms stream of this column contains most of the product ether and excess alcohol present in the reaction zone effluent stream and is passed into a second fractionation column. By proper operation of the second column the entering materials may be separated into a net overhead stream which is an alcohol-ether azeotrope and a bottoms stream of relatively pure product ether which is withdrawn as the product stream of the process. The alcohol-ether azeotrope is preferably recycled to the beginning of the reaction zone. Further details on the separatory method and other aspects of the etherification zone may be obtained from the previously cited references.

After the hydrocarbon recycle stream has passed through the sorption zone and any optional hydrotreating zone employed in the process, the recycle stream is passed into a fractionation zone. Preferably this fractionation zone comprises a single fractionation column but two or more columns could be employed if desired. This column is normally referred to as a deisobutanizer. The recycle stream should enter the column at an upper intermediate point. The isoparaffin component of the recycle stream and the feed stream becomes concentrated into the net overhead stream of the column and is passed into the dehydrogenation zone. The corresponding normal paraffins are removed from the column as part of a lower sidecut stream which is preferably passed into the optional paraffin isomerization zone. The overhead stream of the column should be rich in the isoparaffin and the sidecut stream should be rich in the normal paraffin. As used herein the term "rich" is intended to indicate that the process stream contains at least 55 mole percent of the particular chemical compound or class of compounds which is specified.

The isobutane-rich overhead stream of the deisobutanizer is passed into a butane dehydrogenation zone. This zone will contain a reaction zone and associated auxiliary process equipment such as condensers and a vapor-liquid separator which receives the partially condensed reactor effluent stream. The dehydrogenation zone preferably contains at least one fractionation column. For MTBE production this column is designed and operated to eliminate all ethane and lighter boiling components from the net dehydrogenation zone effluent stream. It may also separate some and possibly all of the propylene into the light ends stream removed from this zone. The propylene may result from the dehydrogenation of propane present in the feed stream to the process or from the cracking of butanes in the production of the light ends removed from this zone. A hydrogen-rich gas stream is separated from the liquid condensed from the reactor effluent. A portion of this gas will normally be recycled and the remainder will be drawn off as a net hydrogen product gas stream. The reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,706,536; 3,825,116; 3,839,196; 3,839,197; 3,854,887, 3,856,662 and 3,978,150.

The particular dehydrogenation conditions employed within the reaction zone may vary depending on such factors as the catalyst activity, feed carbon number and the desired conversion. The reaction zone conditions normally employed for butane dehydrogenation include a temperature of from about 500° to 700° C., a pressure of from 0.5 to about 10 atmospheres and a liquid hourly space velocity of about 1 to 20. The preferred operating temperature will be within the range of from about 550° to 660° C., and the preferred operating pressure is about 0.5 to 2 atmospheres. The preferred butane dehydrogenation catalyst is comprised of a platinum group component, a tin component and an alkali metal component with a porous inorganic carrier material. Other catalytic compositions may be used within this zone if desired. The preferred catalyst contains an alkali metal component chosen from cesium, rubidium, potassium, sodium, and lithium. The preferred alkali metal is normally chosen from lithium and potassium, with potassium being preferred for isobutane. The preparation and use of dehydrogenation catalysts is well known to those skilled in the art and further details as to suitable catalyst compositions is available in patents and other standard references.

To increase the supply of isobutane available to the process and also to convert the nonreactive normal paraffins of the recycle stream, the normal butane-rich deisobutanizer column sidecut stream is preferably passed into a butane isomerization zone. This zone comprises a reactor and auxiliary process equipment such as heaters, condensers, separatory vessels, etc. The isomerization zone preferably also contains a stripping column which eliminates light ends (hydrogen, methane, ethane) from the net effluent of the isomerization zone. With the preferred catalyst, this stripping column will also remove volatile chloride compounds from the isomerization zone effluent. The core of the operation of this zone is passage of the sidecut stream through a reactor maintained at butane isomerization-promoting conditions including the presence of an acidic isomerization catalyst. This is normally a relatively low pressure operation performed at a pressure of from about 50 to 600 psig and at an elevated temperature as required by the activity of the catalyst. The average reactant temperature may be as high as 500° C., but is preferably between 100° and 320° C. It is normal practice to pass the butane through the reactor in admixture with between 1 and 10 moles of hydrogen per mole of butane to ensure vapor phase conditions and to suppress coke deposition on the catalyst. It is preferred that the butane is passed vertically through one or more fixed beds of catalyst located within the reactor at a liquid hourly space velocity between 1.0 and 6.0, but space velocities in the broad range of 0.5 to 12.0 can be employed if desired. The effluent of the isomerization reactor is normally separated into a hydrogen-rich recycle gas which is returned to the reactor and an isomerate-containing liquid stream which is passed into the deisobutanizer column. It is within the scope of the inventive concept that this liquid stream may be further fractionated within the isomerization zone to allow the recycling of normal butanes and the achievement of higher conversion rates, but this is not preferred. The net hydrocarbon effluent of the isomerization zone is a mixture of isobutane and normal butane. This stream should contain 50 mole percent isobutane. Preferably this stream comprises 55 or 60 mole percent isobutane. Further details on the butane isomerization step of the subject process may be obtained by referring to the previously cited references.

The preferred isomerization-promoting catalyst for use in the isomerization zone comprises a platinum group component and a halogen component supported by an inorganic oxide carrier. The preferred platinum group components are platinum and palladium or a mixture of platinum and palladium, with platinum being especially preferred. A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350° to about 700° C. are usually satisfactory. The calcined composite is then reacted with a metal halide of the Friedel-Crafts type. Suitable metal halides include aluminum chloride, aluminum bromide, ferric chloride and zinc chloride, etc. Of these, aluminum chloride is particularly preferred.

I claim as my invention:

1. A process for the production of methyl tertiary butyl ether which comprises the steps of:
   (a) contacting methanol and a mixed hydrocarbon stream comprising normal butane, isobutane and isobutylene with an acidic etherification catalyst to result in the production of methyl tertiary butyl ether, which is removed in a product stream and a recycle stream comprising isobutane, normal butene, water, butadiene, methanol and methyl tertiary butyl ether;
   (b) withdrawing said recycle stream, which is rich in $C_4$ hydrocarbons, and comprises said isobutane, normal butene, water, butadiene, methanol and methyl tertiary butyl ether from the etherification zone;
   (c) contacting said recycle stream with a sorbent solid selected from the group consisting of a Type 5A and Type 13X molecular sieve to remove said methanol and methyl tertiary butyl ether from the recycle stream;
   (d) separating said recycle stream in a deisobutanizer into at least a first stream comprising isobutane which is passed into a dehydrogenation zone to produce isobutylene, said isobutylene being passed into said etherification zone of step (a); and,
   (e) intermittently regenerating said Type 5A or Type 13X molecular sieve by contact with a regeneration gas stream consisting essentially of at least 85 mole percent hydrogen at an initial temperature of below 200° F. and gradually increasing said contact temperature at a rate less than about 50° F. until a temperature in excess of about 400° to 600° F. is reached.

2. The process of claim 1 further characterized in that sulfur-containing compounds and water are also removed from the recycle stream by contact with the sorbent.

3. The process of claim 1 further characterized in that less than 5 mole percent of the butadiene present in the recycle stream is removed from the recycle stream by contacting with said sorbent.

4. The process of claim 3 further characterized in that the recycle stream is also separated into a second stream comprising normal butane which is passed into a butane isomerization zone.

* * * * *